United States Patent [19]

Griffin et al.

[11] Patent Number: 4,878,898
[45] Date of Patent: Nov. 7, 1989

[54] THERMODILUTION AND PRESSURE TRANSDUCER BALLOON CATHETER

[75] Inventors: Joseph C. Griffin, Atco; James L. Skaggs, Indian Mills, both of N.J.

[73] Assignee: Nova Medical Specialties, Indian Mills, N.J.

[21] Appl. No.: 245,623

[22] Filed: Sep. 16, 1988

Related U.S. Application Data

[63] Continuation-in-part of Ser. No. 85,551, Aug. 17, 1987, abandoned.

[51] Int. Cl.[4] .......................................... A61M 29/00
[52] U.S. Cl. ..................................... 604/101; 128/675
[58] Field of Search .................... 604/96, 53, 280, 101; 128/675, 642

[56] References Cited

U.S. PATENT DOCUMENTS

| 2,892,458 | 7/1956 | Auzin | 604/96 |
| 2,976,865 | 3/1961 | Shipley | 128/675 |
| 3,710,781 | 1/1973 | Huthcins, IV et al. | 128/675 |
| 3,866,599 | 2/1975 | Johnson | 604/96 |
| 3,913,565 | 10/1975 | Kawahara | 604/96 |
| 3,995,623 | 12/1976 | Blake et al. | 128/642 |
| 4,329,993 | 5/1982 | Lieber et al. | 604/96 |
| 4,413,528 | 11/1983 | Hok et al. | 128/675 |
| 4,554,927 | 11/1985 | Fussell | 128/607 |

FOREIGN PATENT DOCUMENTS 1262503 3/1968 Fed. Rep. of Germany ...... 128/675

OTHER PUBLICATIONS

*Mechanical Engineering*, "Tiny Heart Probes", Mar. 1968, p. 53.
Lars H. Lindstrom, *BioMedical Engineering*, vol. 17, No. 3, Jul., 1970, pp. 207-219, "Miniturized Pressure Transducer Intended for Intravascular Use".
D. T. Deply, *BioMedical Engineering*, vol. 10, No. 1, Jan., 1975, "A Catheter-Tip Capacitance Pressure Transducer", pp. 16-20.

Primary Examiner—John D. Yasko
Attorney, Agent, or Firm—Shoemaker and Mattare, Ltd.

[57] ABSTRACT

A multi lumen balloon catheter suitable for pulmonary artery catheterization incorporating both pressure and temperature measurement functionalities by means of a forward facing transducer strain gauge device located axially of the inflated balloon for pressure measurement and means for sensing the temperature of the fluid surrounding the exterior of the catheter in use.

7 Claims, 4 Drawing Sheets

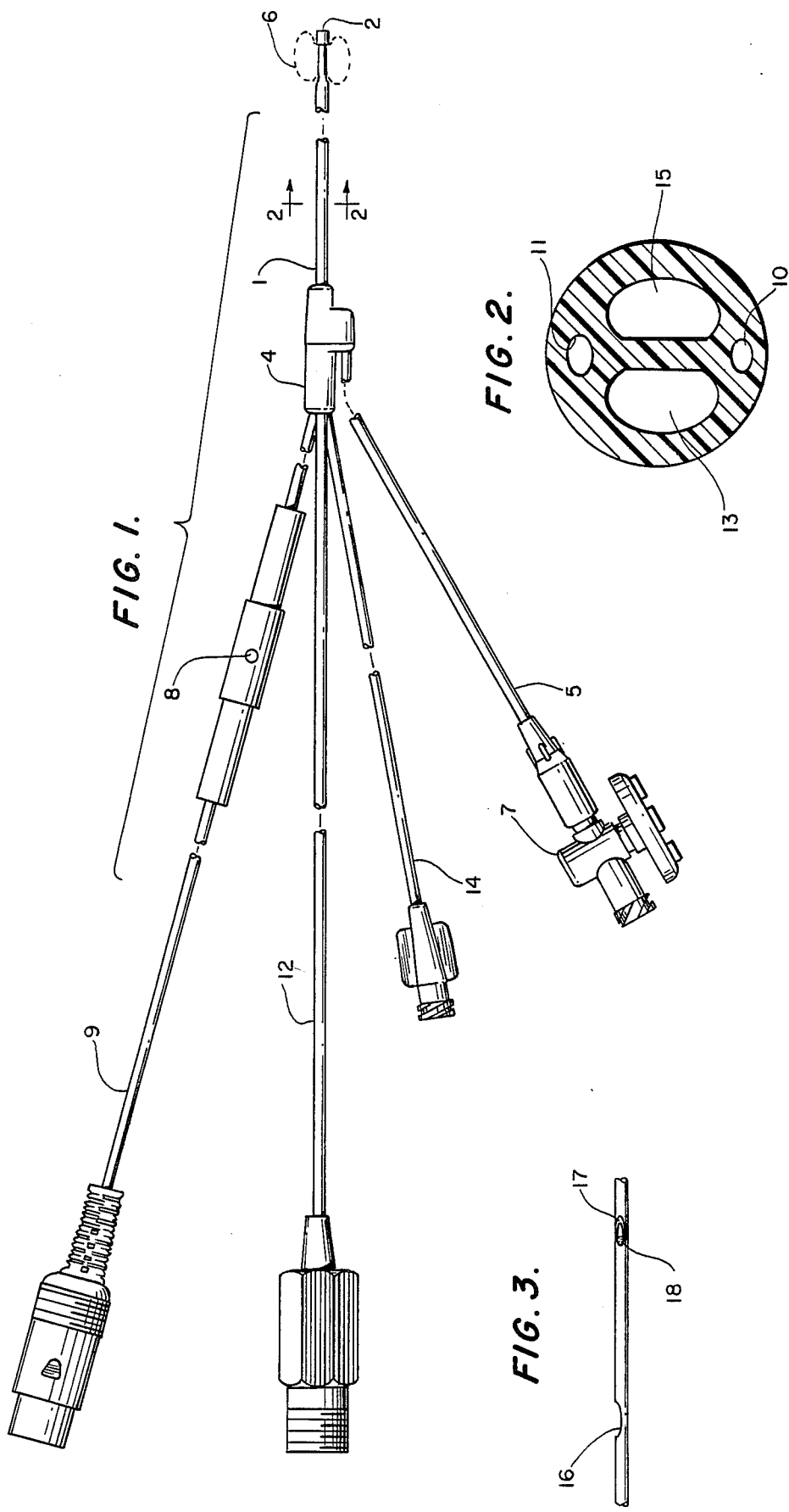

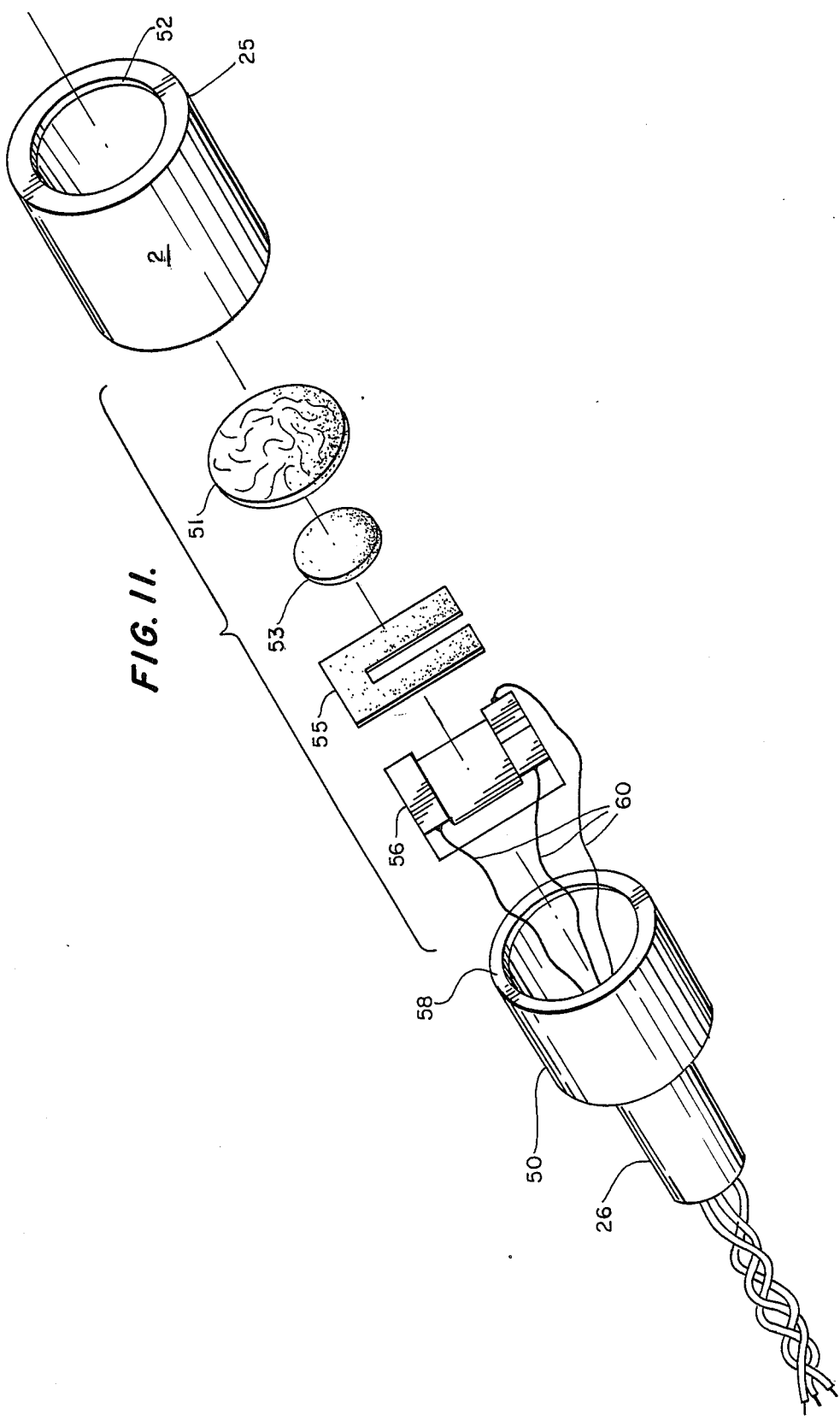

THERMODILUTION AND PRESSURE TRANSDUCER BALLOON CATHETER

BACKGROUND OF THE INVENTION

1. Field of the Invention

The present invention pertains to balloon catheters which are useful in performing pulmonary artery catheterization and more particularly to disposable multi-lumen balloon catheters containing an axial facing pressure transducer which are capable of reproducably and accurately measuring intravascular and intracardiac pressure precisely as well as being capable of being used for thermodilution studies.

2. Description of the Prior Art

Typically, balloon catheters such as the Swan-Ganz thermodilution catheter have been used to obtain certain important cardiac diagnostic information. A single catheter insertion could be used for measuring pulmonary artery and pulmonary capillary wedge pressures, right atrial pressure as well as sampling from either the right atrium or pulmonary artery, as well as injection of a cold bolus solution and detection of temperature change for a determination of cardiac output. In one example of such a catheter which has been widely used, a quadruple lumen seven french catheter body with a balloon at the distal end was structured with a large lumen terminating at the tip of the catheter. This lumen was employed for obtaining pulmonary artery pressure or pulmonary capillary wedge pressure using a fluid coupling. Another lumen terminated in an injection orifice approximately 30 cm proximal to the distal tip of the catheter which provided for injection of cold solution into the right atrium or superior vena cava when the catheter tip was positioned in the pulmonary artery. Central venous pressure could also be measured through this lumen as an alternative to injecting a cold solution. Another lumen was provided for gaseous balloon inflation and the last lumen was provided to carry the electrical leads to the thermistor temperature detector which was exposed at the surface of the catheter about 3.5 cm proximal to the tip.

The direct method of measuring blood pressure provided by the Swan-Ganz catheter employed a hydraulic coupling system which exhibited several disadvantages in use. The principal disadvantage has been termed overshoot since the fluid coupling tended to produce a lag in the measurement which could mask or obscure valuable information and, in some situations, could produce a pressure reading that gave a false indication of a functional condition.

Likewise, movement of the catheter would produce variations in readings from mechanical resonance that could be misinterpreted. Attempts to overcome these problems have been attempted. For example, catheter tip pressure transducers, such as disclosed in U.S. Pat. No. 4,274,423 have employed rectangular cantilever beam type pressure sensitive diaphragms and strain gauges which were sufficiently miniaturized to measure vessel blood pressure radially of the catheter tip. Such devices have utility but are, however, subject to distortions in the pressure readings due to the resiliency of the blood vessel walls adjacent the transducer location, and their design limits their use to catheters without a balloon.

Other devices, such as shown in U.S. Pat. No. 3,550,583 represented attempts to overcome the drawbacks of the previous design for measurement of blood pressure without the use of external hydraulic connectors. The described transducer assembly had limited utility as it was incorporated into an injection needle shape which was not adapted for use in a balloon catheter structure.

In Summary therefore, for pressure recordings, the most widely used systems are fluid-filled catheters and conventional strain-gauge transducer catheters. It is well known that optimal damping of the fluid filled system and adequate frequency response of the transducer are important in obtaining accurate pressure readings. In addition, compliance of the catheter, the length and radius of the catheter, the construction of the pressure transducer, and the materials of construction, and the density and viscosity of the containing fluid are factors determining the frequency response. In particular, air bubbles in the long compliant tubing or stopcock reduce the frequency response. The combination underdamped system and a system that has a low natural frequency results in marked augmentation of the low-frequency components of pressure waves and a distorted wave form and overshoot. Since the fluid column is eliminated in the transducer catheter, the frequency response of the internal and external transducer catheters are superior to that of the fluid filled catheter system.

In conventional transducer systems, the position of the transducer is another important determinant in pressure recordings. If the reference position of the transducer is higher than the position of the chamber from which the pressure is to be recorded, the pressure reading will be lower than actual. Conversely, lowering the transducer artifactually elevates the pressure reading. This problem is eliminated by the internal transducer catheter.

A disposable transducer system has several advantages over the conventional strain gauge transducer. A disposable system is easier to handle and maintain, since the set-up for fluid infusion, long tubing, and potential of air bubbles are eliminated. Furthermore, because the disposable transducer measures the pressures within the desired chamber, careful positioning to obtain a reference point, as with conventional transducers, is not required. Also, the disposable transducer catheter allows the patient's position to be changed while the pressure is monitored and may be useful for ambulatory monitoring of pulmonary arterial pressure. Because of its high frequency response and optimal damping characteristics, it could be useful for measuring the first derivative of right ventricular pressure in the catheterization laboratory.

It has been determined also, that calibration of disposable transducer catheters has posed a serious problem. The materials of construction and the mounting of the strain gauge are sometimes critical to obtaining reproducible base line readings. It is therefore of great importance that the catheter be able to be calibrated to a reproducible base line in use in order to have more confidence in the readings obtained.

It is therefore an object of the present invention to provide a balloon catheter with a axially oriented disposable pressure transducer which in use can provide accurate, nearly instantaneous, reproducible readings of capillary pressure or pulmonary artery occluded pressure during pulmonary artery catheterization and which can also provide accurate, reproducible pressure measurements anywhere in the right side of the heart that can be reached with the catheter.

SUMMARY OF THE INVENTION

The disposable pressure transducer balloon catheter of the present invention is provided with a pressure transducer tip assembly which, in combination with thermodilution study capability provides the objects and advantages of the present invention. A pressure sensor mounted on the distal tip operates on the conventional strain gauge principal. This miniature transducer is designed to function in the vascular system on the tip of a balloon catheter thereby eliminating the hydraulic coupling system necessary with most pressure measuring balloon catheters. The catheter of the present invention will operate in conjunction with other functions of a balloon catheter such as thermodilution studies, blood sampling, or drug infusion or combinations of the foregoing. The pressure transducer is preferably a silicon strain gauge that is characterized by its property of changing electrical resistance as a function of pressure. The strain gauge itself is mounted on a Silicon bridge and both are contained within a stainless steel housing. The strain gauge is releasably contacted on its outward face with a thin stainless steel disc covered by a titanium diaphragm which is exposed to the fluid whose pressure is to be measured. This is contrary to conventionally available structures which employ a stainless steel disc adhesively fixed to the silicon strain gauge and provides for reduced drift in the operation of the transducer. In the preferred embodiment small copper wires connected to the silicon bridge pass through a lumen within the catheter body and are capable of being attached to conventional circuitry for sensing resistance changes in the strain gauge. An interfacing cable designed to match the wires from the transducer to a preselected conventional pressure monitoring equipment, can provide for pressure measurement, and recording. In addition, atmospheric pressure is permitted to communicate to the rear face of the diaphragm by venting the proximal end of the lumen containing the wires and strain gauge to the atmosphere. Thus enables greater reproducability in the zeroing of the transducer.

BRIEF DESCRIPTION OF THE DRAWINGS

FIG. 1 is a side elevation view of one embodiment of the balloon catheter of the present invention.

FIG. 2 is a cross-sectional view of the balloon catheter of FIG. 1 taken at the lines and arrows 2—2 of FIG. 1.

FIG. 3 is a broken section of the distal portion of the catheter of FIG. 1 showing that catheter with thermodilution capability.

FIG. 11 is an exploded view of the strain gauge assembly used in the present invention.

DETAILED DESCRIPTION OF THE INVENTION

Figure 5:
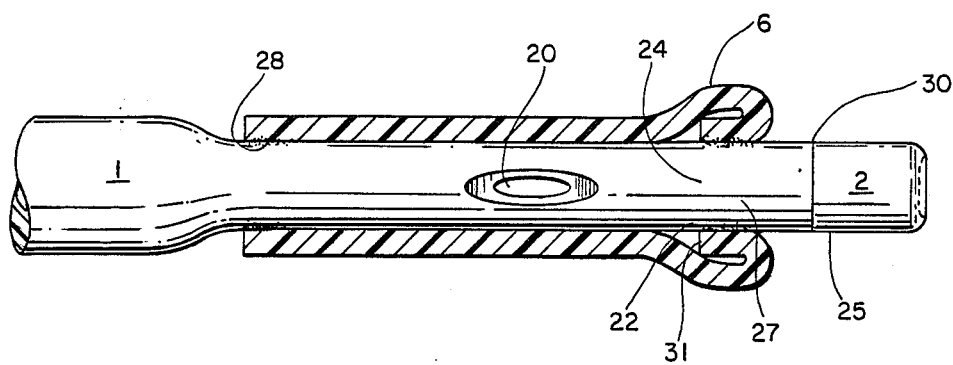
FIG. 5 is a partly broken view of the balloon tip of the catheter shown in FIG. 1 with the transducer in place.

The present invention avoids the drawbacks previously described which were characteristic of the prior catheters employing both direct and indirect measurement techniques. The catheter of the present invention employs a forward facing pressure sensor mounted at the distal tip of a balloon catheter. The pressure sensor, so oriented as shown in the drawings, avoids both the hydraulic coupling systems previously used and the described problems attendant their use, as well as the inaccuracies which can be encountered with the use of laterally facing strain gauge pressure sensors and previous forms of axially oriented strain gauge devices. The pressure readings obtained with the device of the present invention demonstrates no overshooting or mechanical resonance found in conventional catheters with connecting tubing for hydraulic coupling to an external dome transducer or calibration problems encountered in previous internal strain gauges.

Further, the placement or location of the balloon with respect to the transducer at the tip, whose face is substantially perpendicular to the longitudinal axis of the catheter, enables the user greater ease of insertion and manipulation. This contributes to more accurate placement and therefore more precise measurements of direct impact pressure in the wedge position as well as correct direct blood pressure measurements during placement, regardless of the patient's position. Likewise, zeroing of readings after the initial calibration and subsequent calibration to produce reproducible readings is facilitated as will be more fully described hereinafter.

In its preferred embodiment, the catheter of the present invention employs a transducer which comprises a silicon strain gauge housed within an axially oriented stainless steel cylindrical housing containing a forward facing titanium diaphragm, and a stainless steel disc between the diaphragm and the strain gauge. The transducer is connected to copper wires sized to pass through one lumen of the catheter while permitting communication of atmosphere pressure to the rear face of the diaphragm. The strain gauge employed exhibits changes in electrical resistance as a function of pressure. The sensed resistance changes are transformed by conventional equipment, including an impedance matched bridge circuit board, in the catheter, which eliminates the necessity for a gauge factor in calibration, into calibrated pressure readings on appropriate equipment.

FIG. 1 shows a partial plan view of one embodiment of the balloon catheter of the present invention. The catheter body 1 is generally in excess of about 100 cm in length and is extruded from materials which are blood compatible. In addition, the catheter is marked with distance stripes around the catheter at 10 cm interval. These stripes are preferably coded as to number and thickness to represent distance from the distal end of the catheter to enable a visual indication of the depth of the catheter at the insertion site. The transducer assembly 2, described in more detail hereinafter, is disposed perpendicular to the longitudinal axis of the catheter so as to face longitudinally of a vessel instead of laterally. The multiple lumen catheter body terminates at its proximal end with a manifold 4 into which tubes or wires are inserted to communicate with the interior lumens of the catheter body 1 and is provided internally with sufficient hollow space or spaces (not shown) so that appropriate external connections can be provided to each individual lumen of the tubes and the lumens of the catheter body 1.

Referring to FIG. 2, a typical four lumen catheter cross-section is shown. In this embodiment the lumen 10 is provided. When properly connected to a gas supply tube 5, the lumen 10 is thereby provided with means for introducing a source of gas, preferably $CO_2$, to the balloon for inflation, when desired. The supply tube 5 is fitted with a valve means 7 which includes a removable fitting or fixture for closing the balloon 6 from the source of gas (not shown) while in an inflated condition, removing the supply tube 5 from the source of gas, if desired, and controllably releasing the gas pressure inside of the balloon 6 to deflate the balloon when desired.

The lumen 11 in FIG. 2 is provided for accommodating conducting electrical leads and a thermistor for temperature sensing, as will be more fully described hereinafter. Electrical connector and lead assembly 12 is provided to communicate with lumen 11.

Another connector such as a LuerLock ™ type of connector and proximal tube assembly 14 is provided for fluid tight communication with proximal lumen 15 (FIG. 2), whose thermodilution function will be more fully described hereinafter.

Transducer lead and connector assembly 9 is provided for electrical connection with transducer 2 through lumen 13, FIG. 2.

Figure 8:
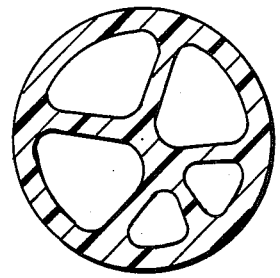
FIG. 8 is a cross-sectional view of a five lumen embodiment of the present invention.
Figure 9:
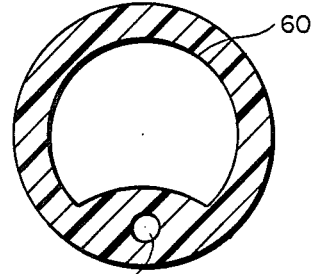
FIG. 9 is a cross-sectional view of a two lumen embodiment of the present invention.
Figure 10:
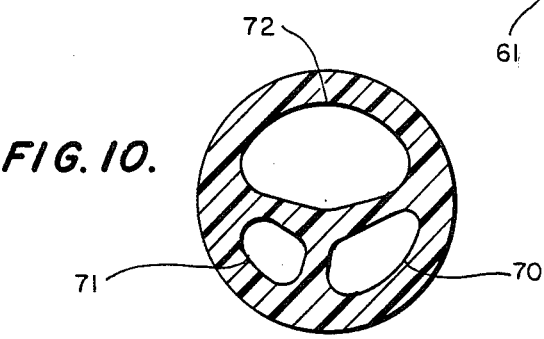
FIG. 10 is a cross-sectional view of a three lumen embodiment of the present invention.

Referring to FIGS. 8, 9 and 10, alternative cross-sectional embodiments of the catheter of the present invention are shown. In FIG. 9, only two lumens are provided. Lumen 60 is provided for accommodating the electrical connections as a transducer assembly 2, and lumen 61 is provided for communicating with a source of gas under pressure for inflating and deflating the balloon 6 as previously described for a four lumen pressure transducer catheter.

In FIG. 10 only three lumens are provided. Lumen 70 is provide for accommodating the electrical connections as a transducer assembly 2, and lumen 71 is provided for communicating with a source of gas under pressure for inflating and deflating the balloon 6 as previously described for a four lumen pressure transducer catheter. Lumen 72 can be used with appropriate connecting assemblies for blood sampling, drug infusion, or combinations of the foregoing or other functions.

In FIG. 8 a typical cross-section of a five lumen catheter is shown. Beside accommodating all of the functions of a four lumen catheter an additional lumen can be used with appropriate connecting assemblies for blood sampling, drug infusion, or other functions as described herein.

Figure 6:
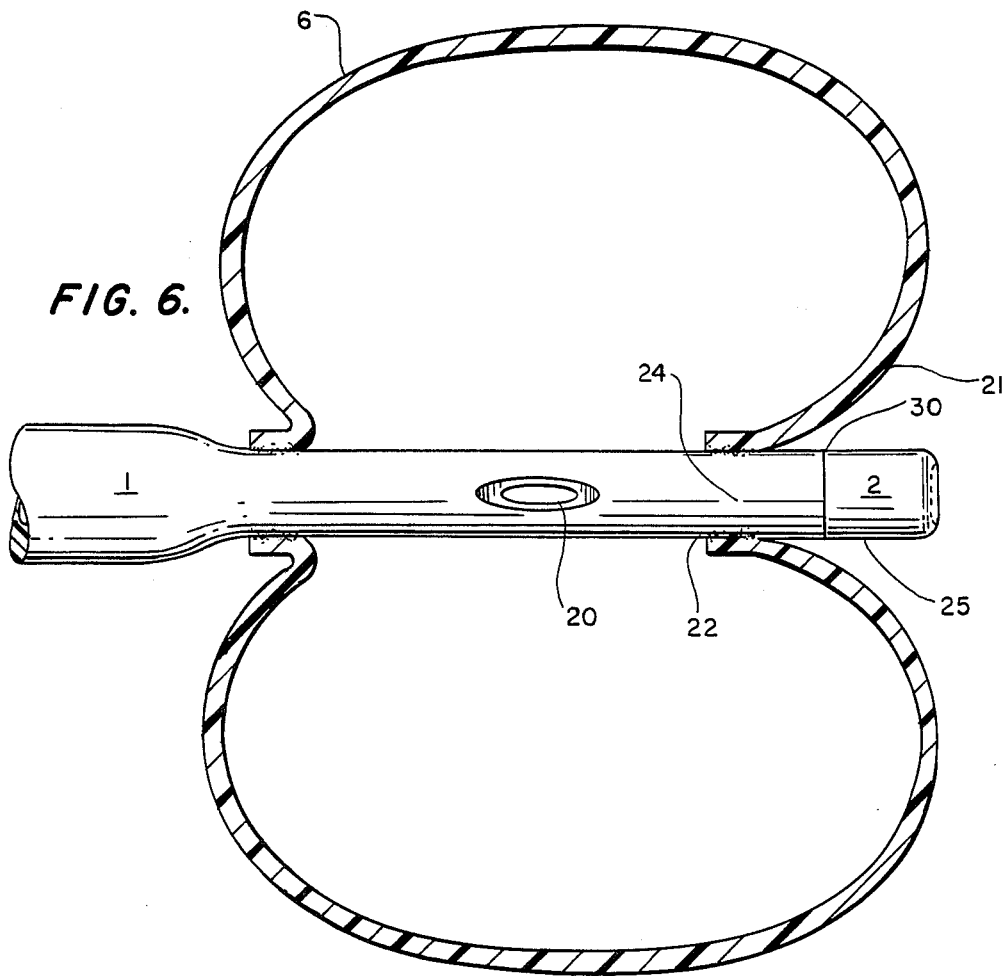
FIG. 6 is a partially sectioned view of the balloon tip shown in FIG. 5 in an inflated or extended position.
Figure 4:
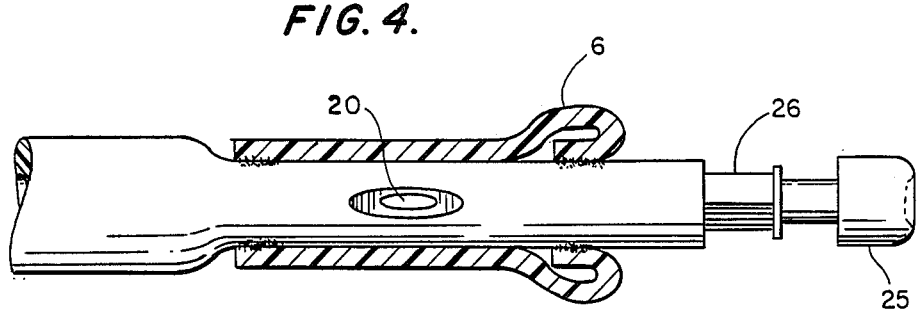
FIG. 4 is a broken partially sectioned view of the balloon tip of the catheter shown in FIG. 1 before the transducer is fully in place.

Referring to FIGS. 4 and 5, the exit opening 20 from lumen 10 is shown exhausting into the space defined by balloon 6. Referring to FIG. 6 the balloon 6 is shown in its approximate fully inflated position which is radially outward of the catheter body 1 and provides an annulus 21 around the housing of transducer 2.

In the inflated condition shown in FIG. 6, the balloon 6 and transducer 2, when positioned in the appropriate locations in a vessel or artery, are uniquely suited for impact and wedge pressure measurements which are obtained in pulmonary artery catheterization for their diagnostic value in evaluating heart function and damage.

The forward or distal end 31 of the balloon sleeve is received onto the catheter tip and then curled back onto itself so that it can be adhesively adhered to the outside of the catheter through what would normally be the outside of the balloon sleeve. The outside of the balloon sleeve is adhesively attached to the necked down portion of the catheter body and then rolled proximally for subsequent adhesive attachment at 28 to the outside proximal portion of the necked down distal tip. The balloon 6 is sized to be large enough to cover the gas lumen opening 20 in a manner which will enable inflation of the balloon in the manner show in FIG. 6. This assembly provides for a balloon configuration, when inflated, which symmetrically aligns the axially oriented transducer 2 within the artery or vessel for more accurate measurement of blood pressure.

The transducer assembly, shown in FIGS. 4, 5, 6 and 11 is made up of very specific materials and in a manner to achieve the benefits and objectives of the present invention described herein. The strain gauge 55 is made of Silicon. The strain gauge bridge 56 is also constructed of Silicon, it being determined that alumina conventionally employed produced objectionable drift in pressure readings. The stainless steel disc 53 which overlays the Silicon strain gauge 55 in use is, in the present invention, not adhesively attached to the Silicon strain gauge 55. Normally such a disc would be adhesively fixed to the gauge 55, however, it was found that this too produced objectionable drift in the pressure readings obtained in use. A titanium diaphragm 51 about 0.0003 in. thick is adhesively affixed at its edges to the inside of the lip 52 of the housing cap 25 and is positioned over the bridge 56, gauge 55 and disc 53 to seal the assembly into the stainless steel housing 50 by the flange 52 on the housing cap 25 firmly seating the titanium diaphragm 51 against the interior edge 58 of the housing 50. The cap 25 and the housing 50 are sized and assembled so that when adhesively fixed together a fluid tight seal is obtained. In this manner no fluids are able to reach the interior of the assembly during normal use.

The strain gauge bridge 56 conventionally was adhesively affixed to the interior of the stainless steel housing 50. This practice has also been eliminated from the structure of the present invention to further reduce drift and contribute to the feature of in use calibration or recalibration. Further, the bridge circuit board in the catheter (not shown) uses matched impedance, preferably about 500 ohms input and output, so that the changes in resistance in the piezoelectric gauge 55 produced by force applied to the titanium diaphragm or disc 51 by blood in use can be displayed by conventional means without a gauge factor. Electrical connections are made to the bridge 56 and the changes in resistance sensed by means of wires 60 which are connected through appropriate connectors attached to connector assembly 9 (FIG. 1). As previously described, the housing extension 26 is adhesively affixed, in a fluid tight manner to the interior of lumen 13 after the distal tip of the catheter body 1 has been necked down as shown in FIGS. 4, 5 and 6. The interior of the housing extension 26 and the communicating lumen is not obstructed by the wires 60 so that there can be atmospheric pressure on the rear face of the disc 51 provided through vent 8 (FIG. 1).

Transducer vent 8 is provided to vent the lumen to the atmosphere. This allows for equalization of pressure on both sides of the silicon strain gauge to reduce the effect of barometric pressure on the measurement of resistance. Zero baseline will not then shift with changes in barometric pressure, and will provide a reproducible base line calibration when used with the low drift transducer assembly construction described herein.

Referring now to FIG. 3 and FIG. 1 of the preferred embodiments of the present invention is provided with the capacity for making thermodilution measurements. Thermodilution is an application of the calorimetric principle that, in a mixture of fluids at different temperatures, the heat lost by one fluid equals the heat gained by the other. For each fluid, the mathematical product of the temperature change, specific heat and mass is equal.

A recognized method for the study of blood circulation involves producing a temperature change in the blood at one point in the blood flow and measuring the temperature change at a second downstream point. Assuming that the measurement of the temperature change occurs at a point downstream of the heat source and that the blood's heat content is uniform, the measured change will reflect the amount of blood passing through the blood vessel.

In thermodilution studies heat is either removed from or added to the blood stream. One technique involves the injection of a cooler saline solution into the blood. In use, a known amount of a cold solution at a known temperature is injected into the right atrium or superior vena cava as through a hole 16 in the catheter 1 body which communicates with a source of fluid at a known temperature and the resultant temperature when mixed with the blood is detected by the thermistor 17 (FIG. 3) while the catheter is placed so that the thermistor 17 is in the pulmonary artery. Cardiac output is inversely proportional to the integral of the observed temperature change. The accuracy of this method is dependent upon the accuracy of the measurement of the temperature of the injectate and the accuracy of the measured temperature of the resultant blood-injectate mixture. Assuming that the blood's heat content is uniform, the measured change in temperature provides a means of calculating the mass of the blood moving in a specific period of time and therefore the amount of blood flowing through the vessel which is a measure of the cardiac output of a particular patient.

Likewise, when properly placed and the balloon deflated, pulmonary artery pressure can be measured by the forward facing strain gauge without the variations that attend the use of fluid coupled pressure measuring devices or side facing strain gauges. The latter experience problems due to the transducer strain gauge diaphragm coming into direct contact with the vessel wall and the variable resilience of the vessel walls which can expand and contract. When the balloon is inflated pulmonary wedge pressure can be recorded and interpreted.

The particular configuration described herein will in addition insure the proper orientation of the transducer diaphragm facing axially of the artery or vein when the balloon is inflated. The inflated balloon is symmetrical and the transducer will be more or less equidistant from the vessel walls.

The connector and tube assembly 14 is provided to join in fluid tight relationship with proximal injection lumen 15, which is provided with a proximal opening 16. The connector and tube assembly 14 is provided with a source of fluid at a known temperature which is injected into the catheter 1 at a known rate and exhausted through proximal opening 16 into the vessel into which the catheter is placed when in use. The lumen 15 is preferably blocked distally of the proximal opening 16. The thermistor opening 17 which communicates with the electrical connector and tube assembly 12 is provided with a plug or seal into which is received a thermistor bead 18 which is connected electrically by wires through the bead lumen 11 to the thermistor bead. The structure is connected to appropriate temperature display means (not shown) by means of electrical connections with the electrical connector and tube assembly 12, to thereby enable a user to calculate the volume of blood flowing by measuring the difference in temperature between the volume of fluid introduced and the temperature of the mixed fluid and blood at the locus of the thermistor bead 18 at the distal locations.

Figure 7:
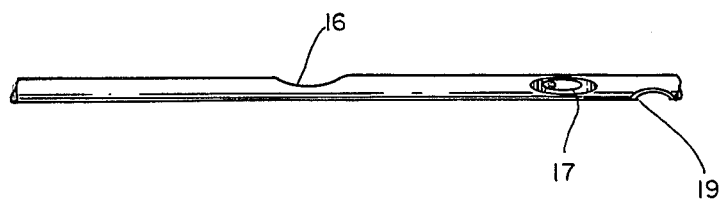
FIG. 7 is a broken view of another embodiment of the catheter of the present invention.

An additional lumen, such as shown in FIG. 8, can be provided to enable infusion of other fluids during the catheterization procedures. FIG. 7 shows the approximate preferred location of such an additional infusion port 19, which is preferably about 2 cm proximal from the distal tip. The thermistor bead 18 is located approximately 3.5 cm proximally from the distal tip.

The overall combination described and illustrated provides a significant improvement in function over the prior external or internal transducer containing catheters and an improvement over the older fluid coupled devices. A pressure transducer catheter produced according to the present invention described herein can measure pressures in the range of from about minus 10 to about 300 mm of Hg, with a zero drift with time of about 1 mm of Hg per 8 hours. The natural frequency response will be about 33 KHz peak and the frequency response from 0 to 4 KHz. Further, a transducer produced as described herein will be relatively unaffected by changes in temperature, having a mean zero drift due to temperature changes of about 0.09 mm of Hg per °C.

It will be appreciated that variations in structure can be employed with the catheter combination described which will be within the scope of this invention which is to be limited only to the appended claims as limited by pertinent prior art.

What is claimed is:

1. A multiple lumen balloon catheter for pulmonary artery catheterization procedures comprising:
   a multiple lumen catheter body having a distal end portion and proximal end portions;
   inflatable balloon means surrounding said distal end portion and including hollow elastic cylindrical sleeve means having inside and outside surfaces, said sleeve means adhesively affixed proximal to said distal end to said catheter body by the inside surface of said sleeve means and adhesively affixed adjacent to the distal end of said catheter body by the outside surface of said sleeve means which has been turned inwardly of the sleeve so as to be inside at least a portion of the inside surface of said sleeve means, and
   transducer means containing housing means having a closed distal end and an open proximal end and capable of being received in fluid tight relationship at the distal end of one of said lumens and adhesively adhered therein, said housing means containing arranged therein a silicon strain gauge bridge within but not fixedly connected to said housing means having wire means electrically connected thereto said wire means communicating through said lumen to the proximal end portion of said catheter body; a piezoelectric Silicon strain gauge means having a front face and a rear face, said rear face being distally contiguous to said strain gauge bridge but not affixed thereto and in electrical contact therewith so that changes in resistance in said piezoelectric strain gauge means can be electrically sensed through the wire means electrically connected to said strain gauge bridge and said wire means, such changes in resistance being proportion to the pressure exerted onto the front face of said transducer means;

force transmitting means closing the distal end of said housing and contiguous to the distal face of said strain gauge means said force transmitting means comprising metal diaphragm means normally in physical contact with said strain gauge means and a titanium diaphragm means located distally of said metal diaphragm means and contiguous thereto, covering said open distal end of said housing means and in fluid tight relationship therewith to form the distal face of said transducer housing means, whereby fluid pressure applied to the titanium diaphragm means transmits a force to said metal diaphragm and onto said strain gauge means to produce a change in resistance that is proportional to said applied force and detectable through the wire means electrically connected to said silicon strain gauge bridge; and said transducer means being located axially of the circumference of said balloon means when said balloon means is inflated.

2. The multiple lumen catheter of claim 1 wherein said multiple lumen catheter further contains infusion means, said infusion means including another of said lumens, and an opening through said catheter body communicating with said lumen of said infusion means communicating with the outside of said catheter body at a first locus proximal to said distal tip and said lumen further provided to communicate with a source of infusion fluid at a second location proximal to said first locus.

3. The multiple lumen catheter of claim 1 wherein said multiple lumen catheter body further contains temperature sensing means said temperature sensing means including at least one additional lumen and an opening through said catheter body communicating with said lumens, and including thermistor means located at the opening to said lumen, said lumen of said temperature sensing means further provided to communicate with a source of infusion fluid at location proximal to said opening.

4. The multiple lumen catheter of claim 3 wherein said thermistor means is located adjacent to the outer periphery of said catheter body at a position distal to said locus of communication of said infusion means lumen with the outside of said catheter body.

5. The multiple lumen catheter of claim 2 wherein said catheter comprises at least four lumens.

6. The multiple lumen catheter of claims 3 wherein said catheter comprises at least five lumens.

7. A multiple lumen balloon catheter for pulmonary artery catheterization procedures comprising:

a multiple lumen catheter body having a distal end portion and a proximal portion;

inflatable balloon means surrounding said distal portion and including hollow elastic cylindrical sleeve means having inside and outside surfaces, said sleeve means adhesively affixed proximal to said distal end to said catheter body by the inside surface of said sleeve means and adhesively affixed adjacent to the distal end of said catheter body by the outside surface of said sleeve means which has been turned inwardly of the sleeve so as to be inside at least a portion of the inside surface of said sleeve means, and transducer means received in the distal end portion of said catheter body and adhesively affixed thereto, said transducer means having a deformable distal face generally perpendicular to the longitudinal axis of said catheter body, said face being capable of being deflected in response to fluid pressure, said transducer means further including piezoelectric Silicon strain gauge means physically communicating with said deformable distal face in a manner so that said gauge means exhibits proportional changes in electrical resistance in response to movements of said deformable distal face caused by the pressure on said deformable distal face, said transducer means being located axially of said balloon means when said balloon means is inflated, and infusion means including at least another of said lumens said infusion means being exposed to the outside of said catheter body proximal to said distal tip for introducing or receiving fluid therethrough, and temperature sensing means in at least one lumen exposed to the outside of said catheter body between said exposed infusion lumen and said distal tip for measuring the temperature of the fluid external to said catheter body at the location of said temperature sensing means.

* * * * *